(12) United States Patent
Castellin et al.

(10) Patent No.: US 8,664,402 B2
(45) Date of Patent: Mar. 4, 2014

(54) PROCESS FOR PREPARING 1-(6-METHYLPYRIDIN-3-YL)-2-[4-(METHYLSULFONYL)PHENYL]ETHANONE, AN INTERMEDIATE OF ETORICOXIB

(75) Inventors: Andrea Castellin, Mestrino (IT); Paolo Stabile, Verona (IT); Francesco Fontana, Longone al Segrino (IT); Ottorino De Lucchi, Padua (IT); Andrea Caporale, Istrana (IT); Stefano Tartaggia, Vallà di Riese Pio X (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 18 days.

(21) Appl. No.: 13/348,371

(22) Filed: Jan. 11, 2012

(65) Prior Publication Data
US 2012/0232281 A1 Sep. 13, 2012

(30) Foreign Application Priority Data

Mar. 9, 2011 (IT) .............................. MI2011A0362
Apr. 15, 2011 (IT) .............................. MI2011A0647

(51) Int. Cl.
*C07D 213/50* (2006.01)

(52) U.S. Cl.
USPC .......................................................... 546/315

(58) Field of Classification Search
None
See application file for complete search history.

(56) References Cited

FOREIGN PATENT DOCUMENTS

| WO | WO 99/15503 A2 | 4/1999 |
|---|---|---|
| WO | WO 99/55830 A2 | 11/1999 |
| WO | WO 01/07410 A1 | 7/2000 |
| WO | WO 01/29004 A1 | 4/2001 |
| WO | WO 03/002118 A1 * | 1/2003 |

OTHER PUBLICATIONS

I. Davies et al., Journal of Organic Chemistry, vol. 65, No. 25, pp. 8415-8420, Sep. 19, 2000 (Abstract).

* cited by examiner

*Primary Examiner* — Zinna Northington Davis
(74) *Attorney, Agent, or Firm* — Dickstein Shapiro LLP

(57) ABSTRACT

A process for preparing 1-(6-methylpyridin-3-yl)-2-[4-(methylsulfonyl)phenyl]ethanone, an intermediate of the synthesis of Etoricoxib. The synthesis of the intermediates useful for such preparation is also described.

23 Claims, 3 Drawing Sheets 6-methylpyridin-3-olo
RN: 1121-78-4 EC: 214-337-8
C6H7NO
109.12588

6-methylpyridin-3-yl trifluoromethansulphonate
RN: 111770-91-3
C7H6F3NO3S
241.18765

(V)

2-methylbut-3-in-2-ol
RN: 115-19-5 EC: 204-070-5
C5H8O
84.11642

5-ethynyl-2-methylpyridin
RN 1945-85-3
C8H7N
117.14788

(IV)

(IV)

1-(6-methylpyridin-3-yl)-ethanone
RN. 36357-38-7 EC: 252-995-8
C8H9NO
135.16316

(II)

(II)
RN 36357-38-7
EC 252-995-8

(II-bis)

4-bromophenyl methyl sulphone
RN: 3466-32-8 EC: 222-421-0
C7H7BrO2S
235.09826

(III, X=Br)

(I)

1-(6-methylpyridin-3-yl)-2-[4-(methylsulphonyl)phenyl]ethanone
RN 221615-75-4
C15H15NO3S
289.3495

US 8,664,402 B2

PROCESS FOR PREPARING 1-(6-METHYLPYRIDIN-3-YL)-2-[4-(METHYLSULFONYL)PHENYL]ETHANONE, AN INTERMEDIATE OF ETORICOXIB

FIELD OF THE INVENTION

The present invention relates to a process for preparing 1-(6-methylpyridin-3-yl)-2-[4-(methylsulfonyl)phenyl]ethanone, an intermediate of the synthesis of Etoricoxib, which is a COX-2 inhibitor pharmaceutical active ingredient.

DESCRIPTION OF THE RELATED ART 1-(6-methylpyridin-3-yl)-2-[4-(methylsulfonyl)phenyl]ethanone of formula (I)

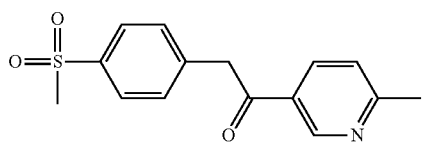

(I)

having CAS RN 221615-75-4 is an important intermediate for the synthesis of Etoricoxib, which is a pharmaceutical active ingredient belonging to the class of COX-2 inhibitors and has been on the market since 2002 with the trade name Arcoxia.

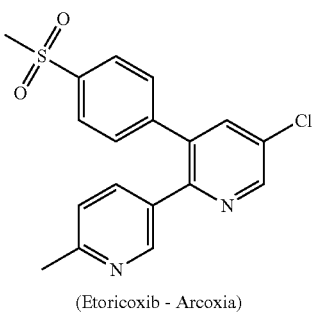 [SMILES: Cc1ccc(-c2ncc(Cl)cc2-c2ccc(S(C)(=O)=O)cc2)cn1]

(Etoricoxib - Arcoxia)

Examples of use of such compound for the synthesis of COX-2 inhibitors are reported in WO 99/55830, WO 99/15503 and by Davies, Lan W et al. in Journal of Organic Chemistry (2000), 65(25), 8415-8420.

Various synthesis methods of such an important building block are known besides those described in the above patent documents, the method described in WO 2001/007410 by Lonza and Merck & Co. seems to be the most advantageous one from the economic point of view. A drawback of such process is that as the last step, it includes an oxidation with hydrogen peroxide catalyzed by sodium tungstate. The subsequent application WO 2001/029004 by Zambon Group S.p.A. describes an improved process for conducting such oxidation which includes the combination of an oxidant (for example, a mixture of peracetic acid and hydrogen peroxide) in the presence of a catalyst (sodium tungstate) and of an acid (for example, methanesulfonic acid).

SUMMARY OF THE INVENTION

The problem addressed by the present invention therefore is to provide an alternative process for preparing 1-(6-methylpyridin-3-yl)-2-[4-(methylsulfonyl)phenyl]ethanone.

Such problem is solved by a process for preparing 1-(6-methylpyridin-3-yl)-2-[4-(methylsulfonyl)phenyl]ethanone, as described in the annexed claims, the definitions whereof are an integral part of the present disclosure.

Further features and advantages of the process according to the invention will result from the following description of preferred embodiments thereof, given by way of a non-limiting example.

DETAILED DESCRIPTION OF THE INVENTION

Figure 1:
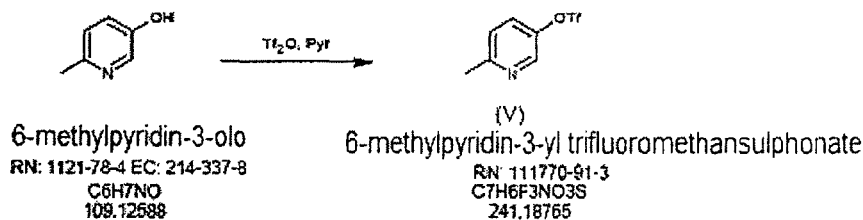
FIG. 1 shows the synthesis scheme 1-(6-methylpyridin-3-yl)-2-[4-(methylsulfonyl)phenyl]ethanone according to the preferred aspects of the present invention.
Figure 1:
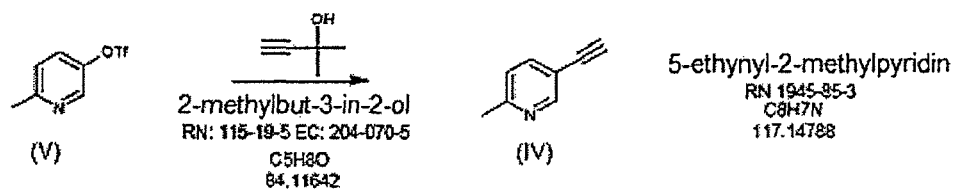
Figure 1:
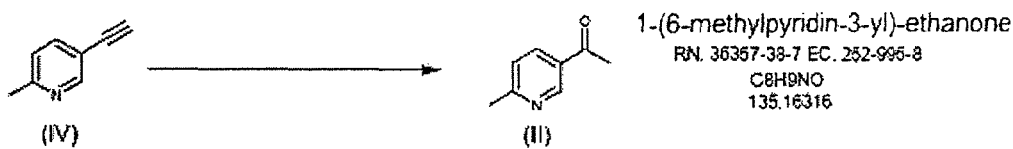
Figure 1:
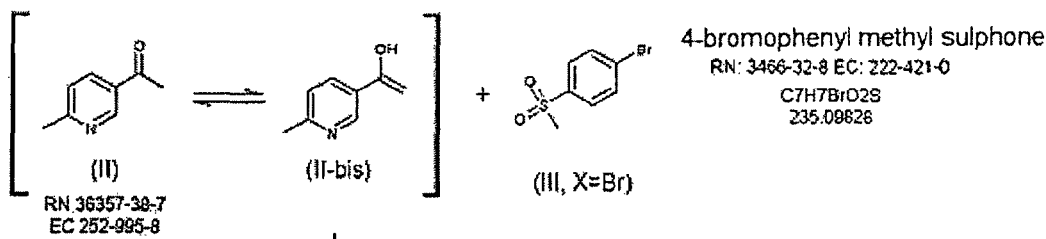
Figure 1:
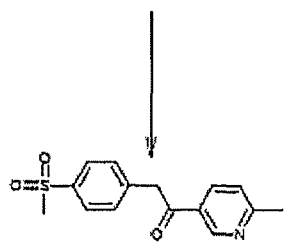

The present invention relates to a process for preparing 1-(6-methylpyridin-3-yl)-2-[4-(methylsulfonyl)phenyl]ethanone of formula (I) or a salt thereof:

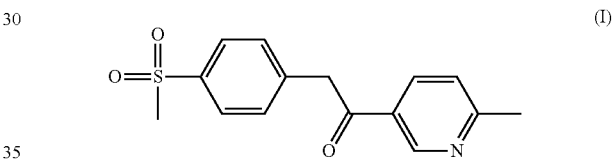

(I)

comprising the reaction of 1-(6-methylpyridin-3-yl)ethanone of formula (II):

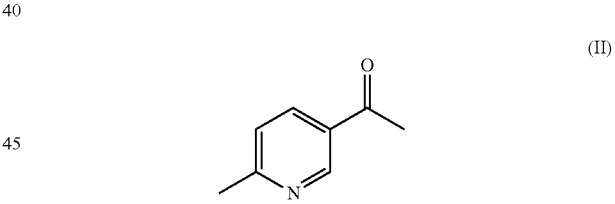

(II)

with the 4-substituted-phenylmethylsulfone of formula (III):

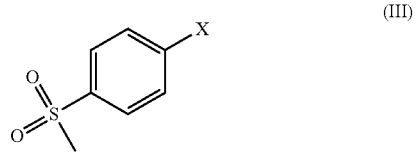

(III)

wherein X is selected from the group consisting of F, Br, Cl, I, OTs, OTf, OMs, ONf and O(C=O)NR$_2$ where R is a linear or branched C1-C4 alkyl substituent, selected from methyl, ethyl, n-propyl, iso-propyl, n-butyl, iso-butyl, sec-butyl or tert-butyl, or is phenyl or benzyl. TsO is the leaving group Tosylate, TfO is the leaving group Triflate, MsO is the leaving group Mesylate, NfO is the leaving group Nonaflate.

In the compound of formula (III), R is preferably ethyl.

According to a preferred aspect of the invention, the process is carried out using 4-bromophenylmethylsulfone.

Also other leaving groups used in couplings of the alpha-arylation type could be used for carrying out such process in replacement of X and should therefore be deemed as an integral part of the present invention.

1-(6-methylpyridin-3-yl)ethanone of formula (II) may also be present in its "enol" form thereof of 1-(6-methylpyridin-3-yl)ethenol of formula (II-bis):

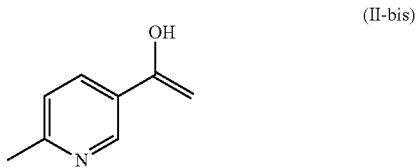

(II-bis)

The process according to the present invention provides for the coupling between the two reagents of formula (II) or (II-bis) and (III) to be carried out according to the reaction conditions illustrated hereinafter.

The reaction is conducted in organic solvent such as toluene, xylene, alcohols or in ether solvents such as dioxane and THF, Me-THF, DMF, DMSO and N-methylpyrrolidone (NMP), ether solvents being preferred and NMP and DMF being even more preferred.

Preferably, the reaction is conducted in 6, 8 or 10 volumes of solvent, preferably 6 volumes.

The reaction is conducted in the presence of a base such as potassium tert-butoxide or potassium carbonate or potassium phosphate, where it is preferably conducted in the presence of potassium phosphate.

An aspect to be noted relates to the milling degree of the base. The milling of potassium phosphate through a wet-miller immediately before the reaction occurs promotes faster reactions and higher yields of desired product.

1 to 3 molar base equivalents are used, preferably 3 molar base equivalents.

The use of 3 base equivalents is preferable to increase the reaction speed and promote a higher conversion of the reagents in the reaction product.

The catalytic precursor used for the reaction is $Pd(OAc)_2$, $Pd(F6-acac)_2$ (Palladium bis(hexafluoro) acetylacetonate) or $Pd(acac)_2$, $Pd_2(dba)_3$, $(PdalkylCl)_2$, $PdCl_2$, $Pd(OAc)_2$ being preferred.

Amounts of catalytic precursor are typically used, comprised between about 0.05% and 2% molar of catalyst referred to 1-(6-methylpyridin-3-yl)ethanone of formula (II), preferably from 0.15% to 0.5% molar.

The ligand used for the reaction is selected from the group comprising $PPh_3$, $P(Cy)_3$, Xantphos, dppe, dppp, dppf, Josiphos, the chelating phosphine Xantphos being preferred.

This is preferably used in amounts comprised between about 0.075% and 1% molar.

Molar amounts of ligand are typically used from 0.5 to 2 times the amount of Palladium catalytic precursor, preferably 2 times (which equals to 1% molar of ligand when the Palladium catalytic precursor is 0.5% molar, always referred to the compound of formula (II)).

For example, in the case of Palladium (II) acetate, the most favorable ligand/metal molar ratio is 0.5, although a ratio of 2 may also be used.

The reaction is conducted between 60° C. and 140° C., preferably between 80° C. and 120° C., more preferably from about 85° C. to about 100° C.

The reaction is typically conducted for 16-30 hours and preferably for about 18-20 hours.

The reaction proceeds with good selectivity since other by-products have not been found, with the exception of small amounts of phenylmethylsulfone resulting from the proto-debromination of 4-bromophenylmethylsulfone.

According to a further preferred aspect, the reaction is conducted in an anhydrous milieu.

The product is then isolated by the conventional organic synthesis techniques comprising extractions and crystallizations.

According to an embodiment of the present invention, the intermediate 1-(6-methylpyridin-3-yl)ethanone of formula (II):

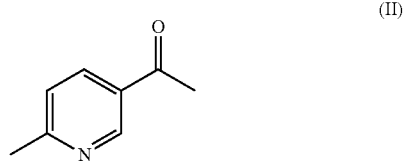

(II)

useful for preparing the compound of the invention may be conveniently prepared by the hydration reaction of 5-ethynyl-2-methylpyridine of formula (IV):

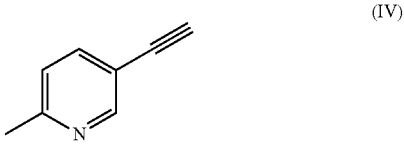

(IV)

Such hydration reaction may be conveniently conducted in a sulfuric acid and toluene mixture, respectively from 2:1 to 4:1, preferably in a 4:1 mixture, respectively. The reaction is conducted at 50° C. for 16 hours, or it may be conducted at 80° C. for hours, or at 70° C. for 2 hours. The product is extracted from the aqueous phase with ethyl acetate and concentrated to residue after anhydrification.

The typical molar yield of this process is higher than 90%.

According to an embodiment of the present invention, the synthesis of the intermediate 5-ethynyl-2-methylpyridine of formula (IV):

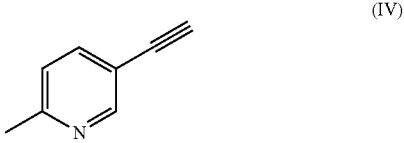

(IV)

useful for preparing the compound of the invention may be conducted by a process comprising the reaction of the intermediate 6-methylpyridin-3-yl trifluoromethansulfonate of formula (V)

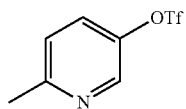

with 2-methyl-3-butin-2-ol.

The reaction is conducted in the presence of Palladium (II) acetate and phosphine. Various phosphines may also be used, such as PPh$_3$, P(p-FPh)$_3$, P(p-tol)$_3$, dppe, dppf, P(p-tol)$_3$ being preferred as it provides higher yields. An NMP/Toluene mixture (1:1) or Toluene only may conveniently be used as organic solvent. The reaction is conducted in the presence of bases such as Pyridine, DBU, Piperidine, HNiPr$_2$, TEA, DABCO, DIPEA.

In a preferred aspect thereof, the reaction is conducted in the presence of piperidine, since it leads to higher yields. The reaction is typically conducted at 40° C. for 16 hours. The compound 2-methyl-4-(6-methylpyridin-3-yl)but-3-in-2-ol is formed as an intermediate of this reaction, optionally easy to isolate, of formula (IV-bis):

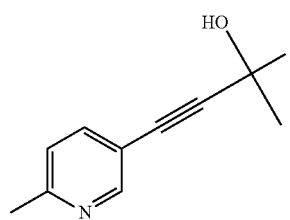

wherein the acetylene function is still protected in the form of acetone adduct. Such protection is removed by a treatment with soda in toluene to reflux for forming the intermediate of formula (IV).

The process for preparing the intermediate of formula (II) starting from the intermediate of formula (V) may also be conducted one-pot, therefore without isolating the compound of formula (IV).

The process for preparing 1-(6-methylpyridin-3-yl)-2-[4-(methylsulfonyl)phenyl]ethanone according to the present invention exhibits the advantage of avoiding the use of tungsten-based catalysts. A further advantage is that the process of the present invention uses intermediates of formula (II) and (III) available on the market and already EINECS registered (at least when X=Br). Moreover, the sulfonate intermediate of formula (III) exhibits the sulfur already in the oxidation state required by the end product, which allows avoiding the final oxidation, therefore, compared to the prior art processes, it allows avoiding the use of hydrogen peroxide and organic peroxides that are potentially explosive hazardous substances. Moreover, such oxidant reagents typically give rise to the reaction by-product pyridine N-Oxide, as described in Journal of Organic Chemistry (2000), 65(25), 8415-8420.

Finally, a further advantage of the process according to the present invention is that the described synthesis path is converging compared to the prior art. The latter involves the sequence of two chemical transformations on the structural core of the desired product. From the point of view of industrial applicability, the process convergence allows isolating the effects of critical process parameters from the quality of the end product.

A variation of the process according to the present invention is that the compound of formula (II) may be reacted with 4-substituted-phenylmethyl sulfide or sulfoxide (III-bis):

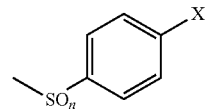

wherein n is respectively 0 and 1 and X has the same meanings above for obtaining respectively compound 1-(6-methylpyridin-3-yl)-2-[4-(methylsulfanyl)phenyl]ethanone of formula (VI):

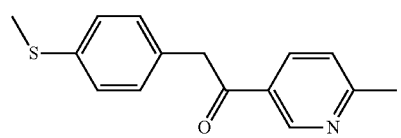

or compound 1-(6-methylpyridin-3-yl)-2-[4-(methylsulfinyl)phenyl]ethanone of formula (VI-bis):

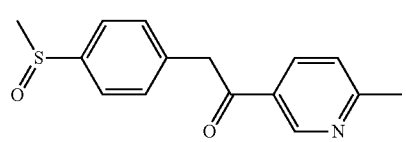

The conditions such as solvents, catalytic precursor, ligands, amounts, etc., to conduct this reaction are analogous to those already described above starting from 4-substituted-phenylmethylsulfone of formula (III), also as regards the preferred aspects.

These intermediate compounds may conveniently be converted into 1-(6-methylpyridin-3-yl)-2-[4-(methylsulfonyl) phenyl]ethanone of formula (I) or into a salt thereof by oxidation of the sulfide or sulfoxide group into sulfone group. Such oxidation is already described in the prior art, for example in J.O.C. 2000, 65, 8415-8420 or in WO 2001/029004 or in WO 2001/007410 by Lonza and Merck & Co. The examination of this last-mentioned document shows that the process of the present invention is particularly advantageous since, the intermediate obtained of formula (VI) being equal, the process of the present invention is much more atom-economy since it is not required to add and then remove the cyan group. This leads to not having to conduct any cyanation reaction, not having to handle industrial amounts of cyanides and preventing the disposal of waste rich in cyanides. Moreover, several synthesis steps are avoided since only two are required. Therefore, even using the process of the present invention wherein a 4-substituted-anisole or a 4-substituted-phenylmethylsulfoxide is used and having then to oxidize the product of formula (VI) or (VI-bis) into the product of formula (I), the process is in any case very advantageous compared to the prior art methods.

In the best case of the process of the present invention wherein 4-substituted-phenylmethylsulfone of formula (III) is used, the compound of formula (I) is obtained with a single synthesis step, thus preventing at least three synthesis steps compared to the known processes and preventing the use and disposal of cyanides. The process of the present invention therefore is very advantageous from the economic point of view.

EXPERIMENTAL PART

Example 1

Synthesis of the intermediate 6-methylpyridin-3-yl trifluoromethansulfonate of formula (V)—Exemplary of the Invention Synthesis scheme

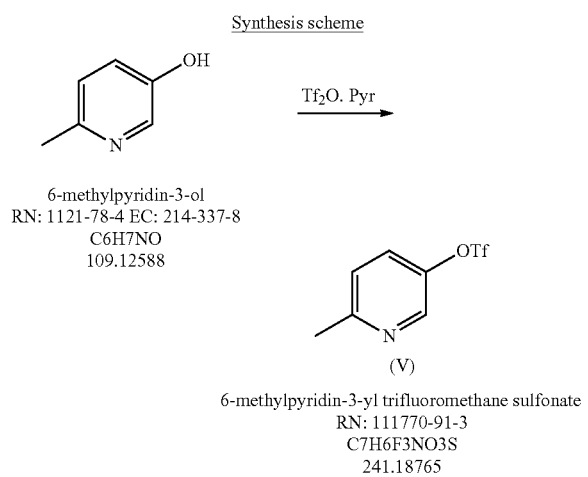

6-methylpyridin-3-ol
RN: 1121-78-4 EC: 214-337-8
C6H7NO
109.12588

6-methylpyridin-3-yl trifluoromethane sulfonate
RN: 111770-91-3
C7H6F3NO3S
241.18765

10.0 g 5-hydroxy-2-methylpyridine (91.7 mmol), 11.0 mL pyridine and 100 mL dichloromethane were loaded into a 250 mL flask provided with mechanical stirrer, thermometer and thermostat. 18.5 mL trifluoromethanesulfonic anhydride (110.0 mmol) were added dropwise to such solution, keeping the temperature at 0° C. After stirring for 1.5 hours, 2 mL MeOH and aqueous solution saturated with NaHCO3 were added. The organic layer was washed with water and brine and then anhydrified on MgSO4. The solution was concentrated to residue under vacuum and the residue was purified on chromatography column using n-Hexane:AcOEt from 9:1 to 4:1 as eluent. 20 g 6-methylpyridin-3-yl trifluoromethansulfonate were obtained, for a molar yield equal to 90.1% as colorless oil.

1H NMR (CDCl3) d 2.61 (s, 3H), 7.26 (d, J=8.4 Hz, 1H), 7.52 (dd, J=9.0, 3.0 Hz, 1H), 8.47 (d, J=3.0 Hz, 1H).

Example 2

Synthesis of the intermediate 5-ethynyl-2-methylpyridine of Formula (IV)—Exemplary of the Invention Synthesis scheme

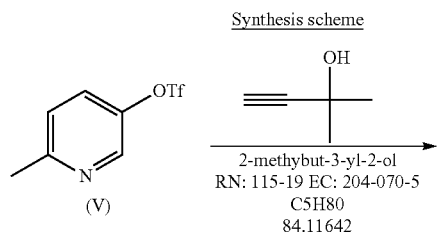

2-methybut-3-yl-2-ol
RN: 115-19 EC: 204-070-5
C5H8O
84.11642

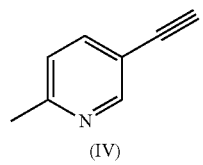

2-ethynyl-2-methylpyridine
RN: 1945-85-3
C8H7N
117.14788

176 mg (0.58 mmol) P(p-tol)3 and 65.0 mg Pd(OAc)2 (0.29 mmol) and 5 mL 6-methylpyridin-3-yl trifluoromethansulfonate of formula (V) (29.0 mmol) were loaded into an anhydrified reactor provided with magnetic anchor. After degassing by argon and vacuum cycles, a solution of degassed pyperidine (11.0 mL, 117.4 mmol) in NMP/Toluene (1:1, 40 mL) was added.

4.2 ml 2-methyl-3-butin-2-ol (43 mmol) were then added with a syringe and the mixture was stirred at 40° C. overnight. After quenching to room temperature, the mixture was diluted with aqueous solution saturated with NaHCO3 (80 mL), then it was extracted with Et2O (3×30 mL). The combined organic extracts were washed with water (50 mL), anhydrified on MgSO4 and concentrated under vacuum at reduced pressure. The oily residue was dissolved in anhydrous toluene (100 ml), then 11.0 g of finely ground NaOH (256 mmol) were added. The solution was heated to reflux for 2 hours, then it was filtered and washed with a saturated solution of NaHCO3 (3×20 mL) and finally anhydrified on MgSO4. The organic phase was concentrated under vacuum, then the raw product was purified by sublimation, thus yielding 2.1 g product for a molar yield equal to 63% as a white solid.

1H NMR (CDCl3) d 2.55 (s, 3H), 3.15 (s, 1H), 7.10 (d, J=7.9 Hz, 1H), 7.64 (dd, J=7.9, 2.13 Hz, 1H), 8.60 (d, J=3.0 Hz, 1H).

Example 3

Synthesis of the intermediate 1-(6-methylpyridin-3-yl)ethanone of formula (II)—Exemplary of the Invention Synthesis scheme

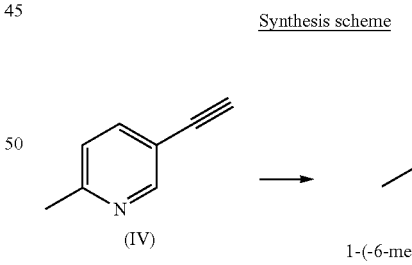

1-(-6-methylpyridin-3-yl)ethanone
RN: 36357-38-7 EC: 252-995-8
C8H9NO
135.16316

1.0 g 5-ethynyl-2-methylpyridine (8.5 mmol) was loaded into a flask provided with magnetic anchor and was dissolved in 10 mL of a 1:4 toluene/sulfuric acid mixture (0.29 mmol). The resulting solution was heated to 50° C. overnight, then after quenching to room temperature, the solution was basified by the addition of NaHCO3, then it was extracted with AcOEt (3×20 mL) and finally, anhydrified on anhydrous MgSO4. The organic phase was then concentrated under vacuum yielding 1.06 g product, equal to a molar yield of 91% as a yellow oil.

Example 4

Synthesis of 1-(6-methylpyridin-3-yl)-2-[4-(methylsulfonyl)phenyl]ethanone of formula (I)—Exemplary of the Invention

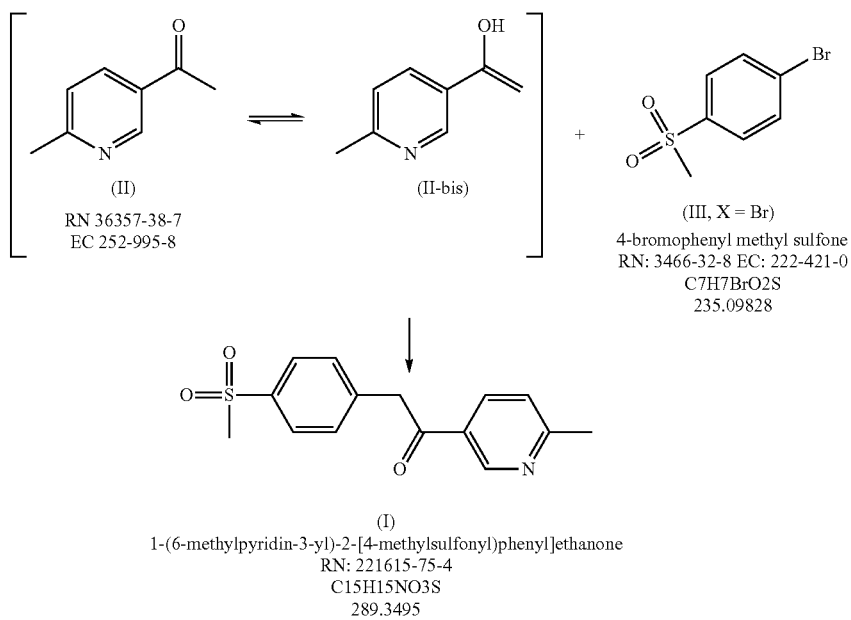

(I)
1-(6-methylpyridin-3-yl)-2-[4-methylsulfonyl)phenyl]ethanone
RN: 221615-75-4
C15H15NO3S
289.3495

A Schlenk reaction tube anhydrified beforehand provided with magnetic anchor was loaded with tri-tert-butyl-phosphonium tetrafluoborate (5.4 mg; 18.5 μmol), Pd(OAc)$_2$ (2.1 mg; 9.2 μmol), 4-bromophenylmethylsulfone (130.4 mg; 0.55 mmol), 1-(6-methylpyridin-3-yl)ethanone of formula (II) (50 mg; 0.37 mmol) and was closed with a septum. The vessel was degassed by 3 argon cycles, then 2 ml anhydrous toluene were added with a syringe. T-BuOK (165.7 mg; 1.48 mmol) was added in portions and the solution was heated to 80° C. for 16 hours. The mixture was diluted with a saturated solution of NaHCO$_3$ (20 mL) and extracted with AcOEt (3×20 mL). The combined organic phases were washed with an aqueous solution saturated with NaHCO$_3$ (20 mL), anhydrified on MgSO$_4$ and concentrated in a vacuum. The residue was purified by flash chromatography using AcOEt/cyclohexane as eluent in a gradient from 5:5 to 10:0. 32.1 mg product were obtained, for a molar yield of 30% as a white crystalline solid.

Figure 2:
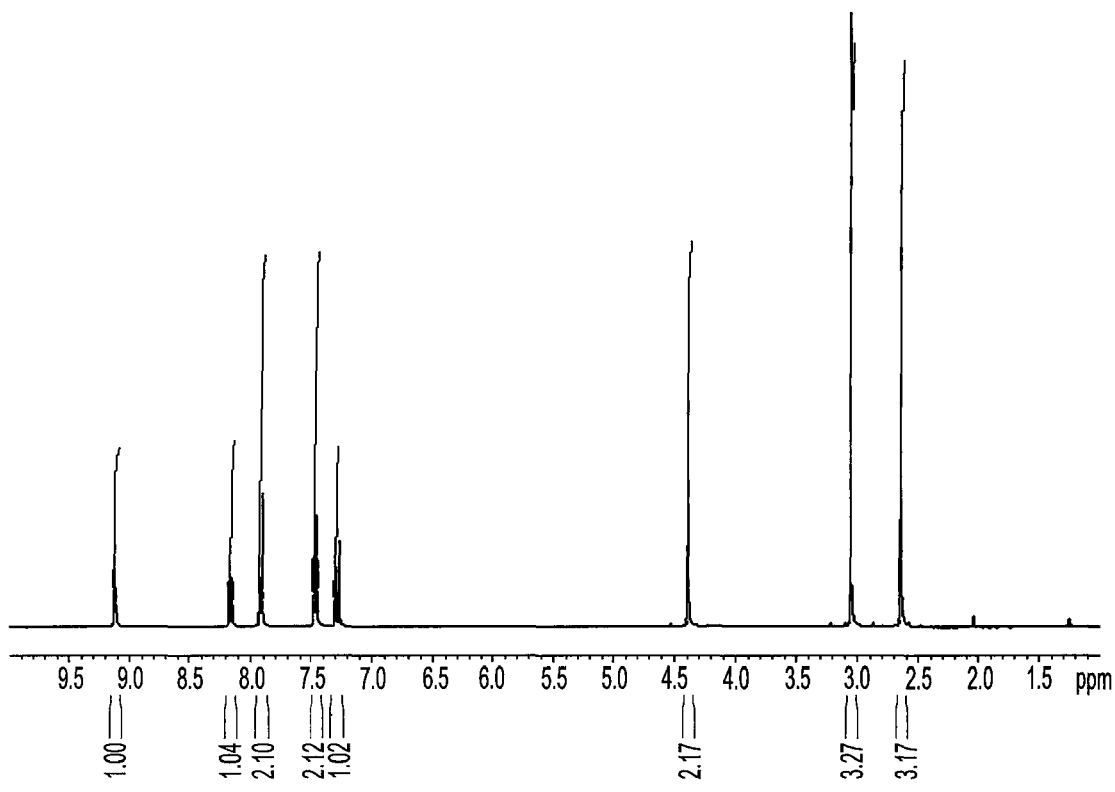
FIG. 2 shows a spectrum 1H-NMR of the product of formula (I) obtained according to the process of the present invention.

1H NMR(CDCl$_2$): 2.64 (s, 3H), 3.04 (s, 3H), 4.38 (s, 2H), 7.29 (d, J=8.2 Hz, 1H), 7.46 (d, J=8.3 Hz, 2H), 7.91 (d, J=8.3 Hz, 2H), 8.16 (dd, J=8.2, 2.2 Hz, 1H), 9.11 (d, J=2.2, 1H) (See FIG. 2).

Example 5

Synthesis of 1-(6-methylpyridin-3-yl)-2-[4-(methylsulfonyl)phenyl]ethanone of formula (I)—Exemplary of the Invention Synthesis scheme

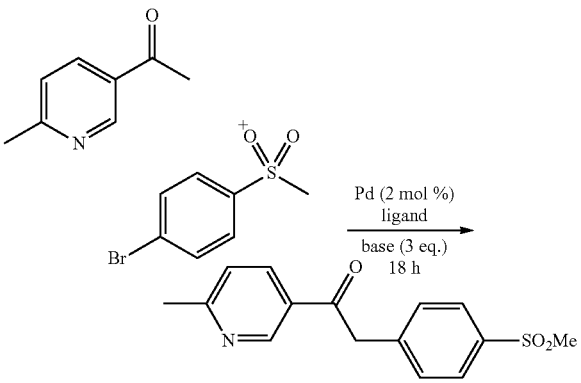

| No. | Solv. | Pd (2%) | Ligand (%) | Base (3 eq.) | T (° C.) | GC Yield (%) |
|---|---|---|---|---|---|---|
| 1 | dioxane | Pd(OAc)$_2$ | PPh$_3$ (4) | tBuOK | 80 | 2 |
| 2 | THF | Pd(OAc)$_2$ | PPh$_3$ (4) | tBuOK | 80 | 7 |
| 3 | toluene | Pd(OAc)$_2$ | PPh$_3$ (4) | K$_3$PO$_4$ | 80 | 24 |
| 4 | THF | Pd(OAc)$_2$ | P(Cy)$_3$ (4) | K$_3$PO$_4$ | 80 | 8 |

-continued

| No. | Solv. | Pd (2%) | Ligand (%) | Base (3 eq.) | T (° C.) | GC Yield (%) |
|---|---|---|---|---|---|---|
| 5 | THF | Pd(OAc)$_2$ | xantphos (2) | K$_3$PO$_4$ | 80 | 46 |
| 6 | NMP | Pd(OAc)$_2$ | xantphos (2) | K$_3$PO$_4$ | 80 | 58 |
| 7 | NMP | Pd(OAc)$_2$ | xantphos (2) | K$_3$PO$_4$ | 100 | 75 |
| 8 | NMP | Pd(OAc)$_2$ | dppe (2) | K$_3$PO$_4$ | 100 | 49 |
| 9 | NMP | Pd(OAc)$_2$ | dppp (2) | K$_3$PO$_4$ | 100 | 27 |
| 10 | NMP | Pd(OAc)$_2$ | dppf (2) | K$_3$PO$_4$ | 100 | 14 |

Example 6

Synthesis of 1-(6-methylpyridin-3-yl)-2-[4-(methylsulfonyl)phenyl]ethanone of Formula (I)—Exemplary of the Invention Synthesis scheme

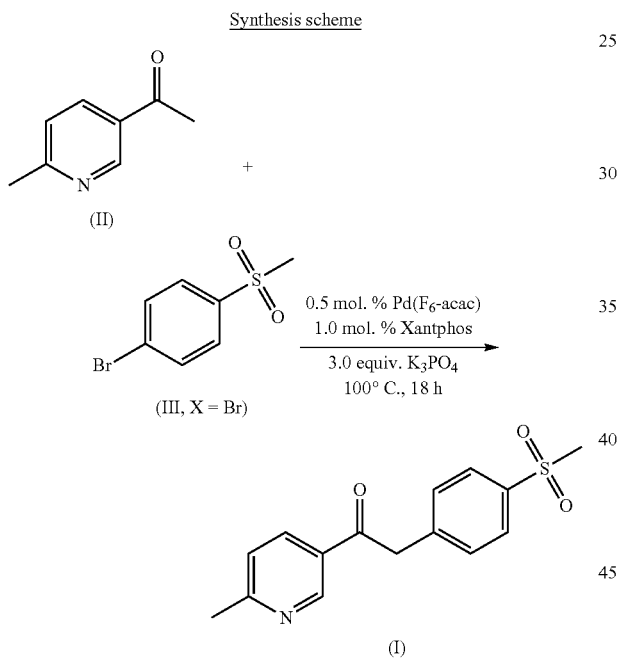

Pd(F6-acac)$_2$ (10.4 mg, 0.02 mmol, 0.5 mol %) and Xantphos (23.2 mg, 0.04 mmol, 1 mol %) are introduced into a flared flask provided with coolant.

4-bromophenylmethylsulfone of formula (III, X═Br) (1.17 g, 5 mmol), acetylpicoline of formula (II) (541 mg, 4 mmol) and K$_3$PO$_4$ (2.55 g, 12.0 mmol, 3 eq) are added thereto. Once the argon atmosphere has been stabilized with vacuum-argon cycles, anhydrous and degassed NMP (15 ml) is added with a syringe. The mixture is kept under stirring in argon atmosphere for 18 h at 100° C. The gas-chromatographic assay shows a yield of 94%.

The reaction mixture is diluted with a solution of 10% ammonium chloride in water (15 ml) and extracted with dichloromethane (2×10 ml). The combined organic phases are filtered on dicalite, washed brine (10 ml) and concentrated at reduced pressure. The resulting reaction raw product is re-crystallized from 10 ml acetone to obtain 974 mg product of formula (I) for a molar yield of isolated product equal to 84%.

Example 7

Synthesis of 1-(6-methylpyridin-3-yl)-2-[4-(methylsulfanyl)phenyl]ethanone of formula (VI)—Exemplary Variant of the Invention

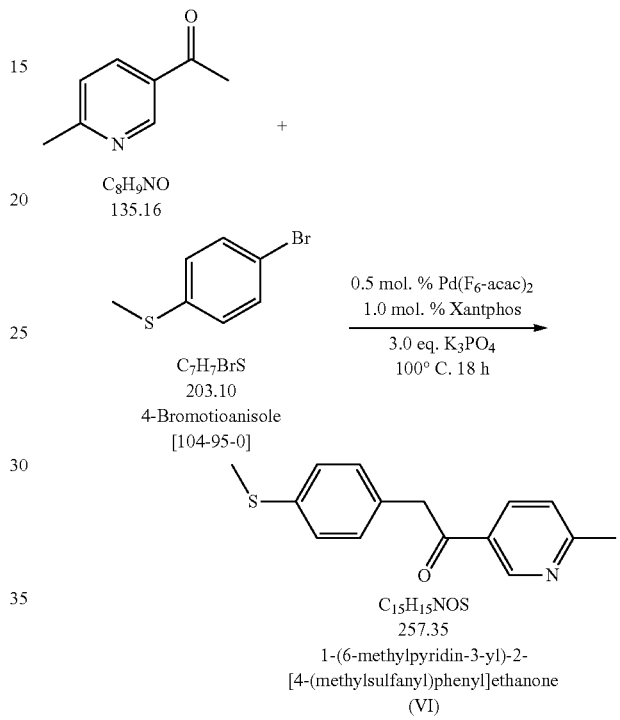

The reaction is conducted as described in Example 6 but using 4-Bromotioanisole in place of 4-bromophenyl-methyl sulfone. The gas-chromatographic assay shows a yield in product of formula (VI) equal to 94%.

Figure 3:
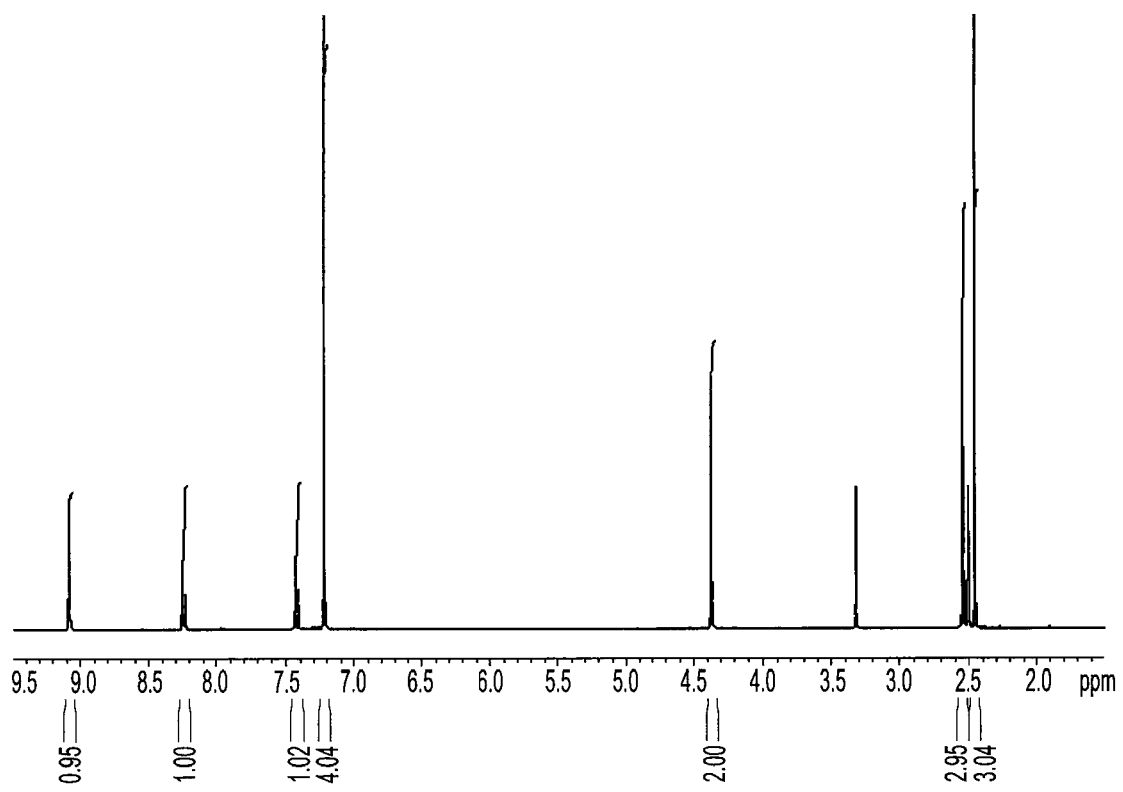
FIG. 3 shows a spectrum 1H-NMR of the product of formula (VI) obtained according to the process of the present invention.

The isolated product H-NMR spectrum is annexed in FIG. 3.

Example 8

Synthesis of 1-(6-methylpyridin-3-yl)-2-[4-(methylsulfonyl)phenyl]ethanone of Formula (I)—

Exemplary Variation of the Invention

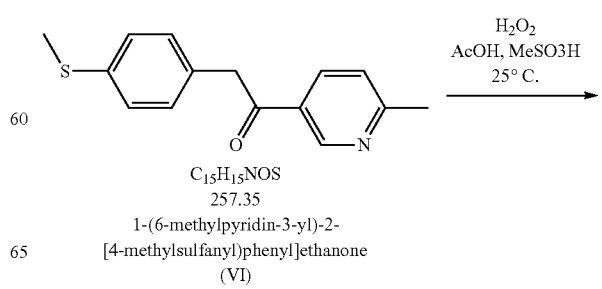

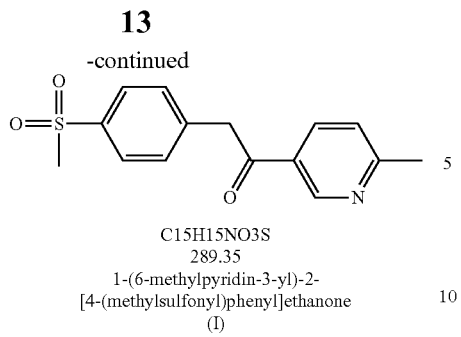

C15H15NO3S
289.35
1-(6-methylpyridin-3-yl)-2-
[4-(methylsulfonyl)phenyl]ethanone
(I)

100 g 1-(6-methylpyridin-3-yl)-2-[4-(methylsulfanyl)phenyl]ethanone of formula (VI) (1.0 equiv.), 150 mL ice-cold acetic acid (1.5 vol) and 30 mL methanesulfonic acid (1.2 equiv, 0.3 vol-96.11 g/mol; 1.481 g/ml) are introduced into a 3000 ml flask provided with high-temperature thermometer, coolant and dropping funnel.

The reaction mixture is quenched to 5-10 ° C.

120 mL hydrogen peroxide 30% w/w (3 equiv, 1.20 vol; 34.02 g/mol: 1.13 g/ml) are added under stirring at 5-10° C. The reaction mixture is stirred at 20-25° C. for at least 6 hours. At the end of the reaction, it is quenched to 0-5° C. and a solution consisting of 300 g sodium thiosulfate (3 wt) and water (10 vol) is added in portions.

Approximately 180-260 ml of an aqueous solution of 30% sodium hydroxide are added up to reach a pH of about 5.5-6.5.

It is stirred at 20-25° C. for 2 h and the suspension is filtered. The solid is washed with 2×400 mL water, then the solid is dried at 40° C. in a vacuum for at least 12 h. 105.7 g product are obtained, for a molar yield of 94% HPLC purity, equal to 97.5% (A %).

Example 9

Synthesis of 1-(6-methylpyridin-3-yl)-2-[4-(methylsulfonyl)phenyl]ethanone of formula (I)—Exemplary of the Invention Synthesis scheme

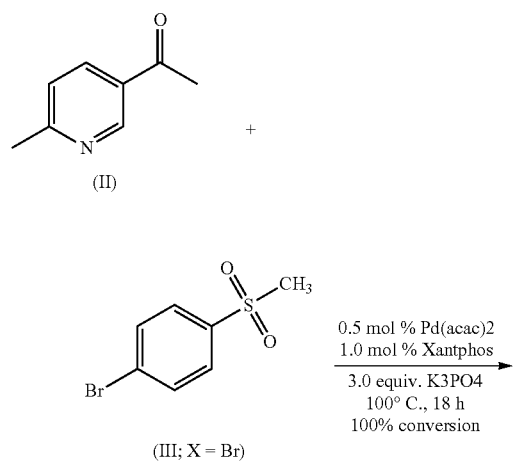

(III; X = Br)

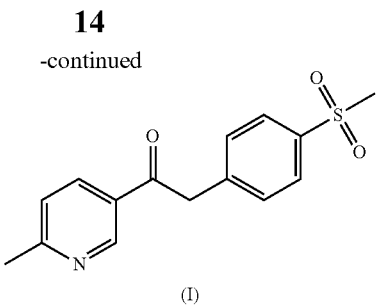

(I)

Pd(acac)$_2$ (6.1 mg, 0.02 mmol, 0.5 mol %) and Xantphos (23.2 mg, 0.04 mmol, 1 mol o) are introduced into a flared flask provided with coolant. 4-bromophenylmethylsulfone of formula (III, X=Br) (1.17 g, 5 mmol), acetylpicoline of formula (II) (541 mg, 4 mmol) and K$_3$PO$_4$ (2.55 g, 12.0 mmol, 3 eq) are added thereto. Once the argon atmosphere has been stabilized with vacuum-argon cycles, anhydrous and degassed NMP (15 ml) is added with a syringe. The mixture is then kept stirred under stirring in an argon atmosphere for 18 h at 100° C. The conversion is quantitative. The reaction mixture is diluted with a saturated solution of NaHCO$_3$ (50 mL) and extracted with AcOEt (4×50 mL). The combined organic phases were washed with an aqueous solution saturated with NaHCO$_3$ (30 mL), anhydrified on MgSO$_4$ and concentrated in a vacuum. The residue was purified by silica gel chromatography using AcOEt/cyclohexane as eluent in a gradient from 5:5 to 10:0. 1.05 g product were obtained, for a molar yield of 91% as a white crystalline solid.

Example 10

Synthesis of 1-(6-methylpyridin-3-yl)-2-[4-(methylsulfonyl)phenyl]ethanone of formula (I)—Exemplary of the Invention According to a Particularly Preferred Embodiment Synthesis scheme

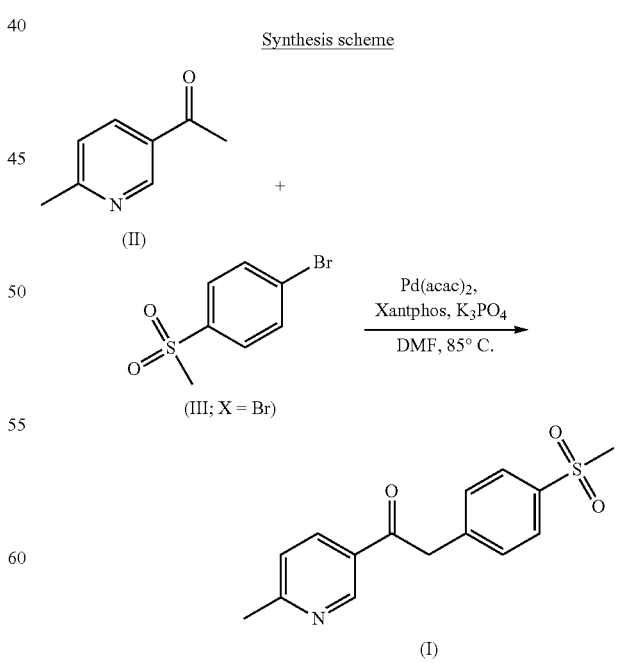

1-(6-methylpyridin-3-yl)ethanone of formula (II) (50 g, 1 equiv, 0.370 mol), 4-bromophenyl-methyl sulfone of formula (III; X=Br) (87 g, 1 equiv, 0.370 mol), potassio phosphate (235.6 g, 3 equiv, 1.110 mol), Pd(acac)$_2$ (169 mg, 0.15 equiv. mol. %), Xantphos (482 mg, 0.225 equiv. mol. %) and N,N'-dimethylformamide (300 ml) were introduced into a 2000 ml flask at 20-25° C. and under a nitrogen atmosphere. After having carried out three cycles of vacuum and nitrogen, the reaction mixture was heated to 85° C. and stirred at such temperature under a nitrogen atmosphere for 20 h. The reaction mixture was then quenched to 50° C. and diluted with water (800 ml). The resulting mixture was stirred for 15 min at 50° C., then the lower aqueous phase was separated by siphoning. The residue was diluted with water (600 ml), quenched to 0-5° C. and stirred at such temperature for 2 h. The resulting mixture was filtered and the solid was washed with water (4×200 ml) and dried at 65° C. for 10 h, yielding 95.3 g 1-(6-methylpyridin-3-yl)-2-[4-(methylsulfonyl)phenyl]ethanone (molar yield=89%).

It should be noted that in this case, the reaction proceeds in a manner almost similar using the same amount of ligand in terms of molar equivalents relative to the Palladium catalyst, that is, 0.15% molar equivalents relative to the substrate of formula (II).

Example 11

Synthesis of 1-(6-methylpyridin-3-yl)-2-[4-(methylsulfonyl)phenyl]ethanone of formula (I)—Exemplary of the Invention According to another Very Particularly Preferred Embodiment Synthesis scheme

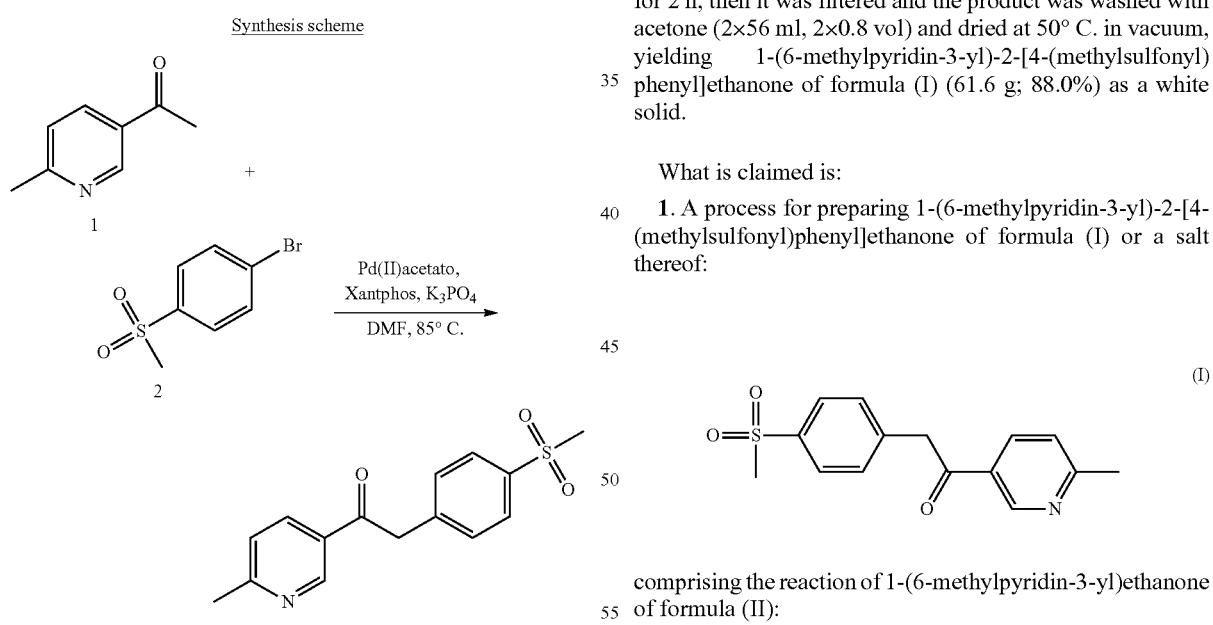

1-(6-methylpyridin-3-yl)ethanone 1 (50 g, 370 mmol), 1-bromo-4-(methylsulfonyl)benzene 2 (87 g, 370 mmol), potassium phosphate (235.6 g, 3 equiv, 1.11 mol), palladium (II) acetate (125 mg, 0.15mol, 557 μmol), Xantphos (161 mg, 0.075% mol, 278 μmol) and N,N'-dimethylformamide (300 ml, 6 vol) were introduced in the order into a 2000 ml flask provided with mechanical stirring, thermometer and coolant, at 25° C. and under a nitrogen atmosphere. The reaction mixture was stirred at 25° C. and subject to three cycles of vacuum and nitrogen, then it was heated to 85° C. and stirred at such temperature for 27 h. The reaction mixture was then quenched to 45° C. and the stirring was stopped, promoting the separation of an aqueous phase that was removed by suction siphoning with the aid of vacuum. The resulting higher mixture was diluted with water (600 ml, 12 vol) and was quenched to 3° C. After 2 h stirring at such temperature, the resulting suspension was filtered and the product was washed with water (4×200 ml, 4×4 vol) and dried at 60° C. in vacuum, yielding the raw 1-(6-methylpyridin-3-yl)-2-[4-(methylsulfonyl)phenyl]ethanone of formula (I) (89.1 g, 83.2%) as a yellow solid.

The raw 1-(6-methylpyridin-3-yl)-2-[4-(methylsulfonyl) phenyl]ethanone of formula (I) (80 g) thus obtained was dissolved in a mixture of dichloromethane (560 ml, 7 vol) and HCl 0.5 M (384 ml, 4.8 vol). The separated organic phase was repeatedly extracted with HCl 0.5 M (2×192 ml, 2×2.4 vol and 96 ml, 1.2 vol). The combined aqueous phases were neutralized by the addition of NaOH 15% (91 ml, pH 6.8) and the resulting aqueous mixture was quenched to 15° C. and stirred at such temperature for 2 h. The resulting suspension was filtered and the product was washed with water (4×320 ml, 4×4 vol) and dried at 65° C. in vacuum, yielding the compound of formula (I) purified (71.7 g; 89.6%) as a straw-yellow solid.

The purified 1-(6-methylpyridin-3-yl)-2-[4-(methylsulfonyl)phenyl]ethanone of formula (I) (70 g) obtained as described above was dissolved at 120° C. in N,N'-dimethylformamide (84 ml, 1.2 vol). The resulting solution was quenched at 25° C. Product crystallization is observed during the quenching. The resulting suspension was stirred at 25° C. for 2 h, then it was filtered and the product was washed with acetone (2×56 ml, 2×0.8 vol) and dried at 50° C. in vacuum, yielding 1-(6-methylpyridin-3-yl)-2-[4-(methylsulfonyl) phenyl]ethanone of formula (I) (61.6 g; 88.0%) as a white solid.

What is claimed is:

1. A process for preparing 1-(6-methylpyridin-3-yl)-2-[4-(methylsulfonyl)phenyl]ethanone of formula (I) or a salt thereof:

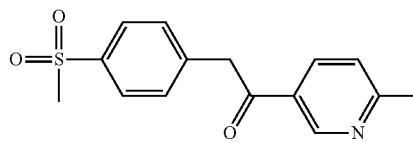

(I)

comprising the reaction of 1-(6-methylpyridin-3-yl)ethanone of formula (II):

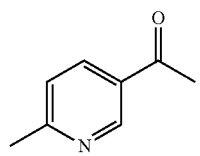

(II)

with the 4-substituted-phenylmethyl sulfone of formula (III-bis):

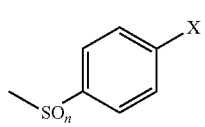

(III-bis)

wherein n is 2 and X is selected from the group consisting of F, Br, Cl, I, OTs, OTf, OMs, ONf and O(C=O)NR$_2$ where R is a linear or branched C$_1$-C$_4$ alkyl substituent or it is phenyl or benzyl.

2. A process according to claim 1, wherein the compound of formula (III-bis) has n equal to 2, that is, has formula (III):

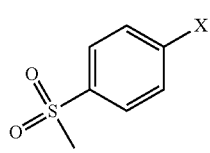

(III)

wherein X has the same meanings as in claim 1.

3. A process according to claim 1, wherein X is bromine.

4. A process according to claim 1, wherein the reaction is conducted in organic solvent selected from the group comprising toluene, xylene, alcohols, ether solvents including dioxane and THF, Me-THF, DMF, DMSO and NMP or the solvent is THF or NMP or DMF.

5. A process according to claim 1, wherein the reaction is conducted in the presence of a base selected from potassium tert-butoxide and potassium phosphate.

6. A process according to claim 1, wherein 1 to 3 molar base equivalents are used, or 3 molar base equivalents are used.

7. A process according to claim 1, wherein the reaction is conducted in the presence of a catalytic precursor selected from Pd(OAc)$_2$, Pd(F6-acac)$_2$ and Pd(acac)$_2$ or it is Pd(OAc)$_2$.

8. A process according to claim 1, wherein an amount from 0.05% to 2% molar of catalyst relative to the substrate of formula (II) is used in the reaction.

9. A process according to claim 1, wherein an amount from 0.15% to 0.5% molar of catalyst relative to the substrate of formula (II) is used in the reaction.

10. A process according to claim 1, wherein the reaction is conducted in the presence of a binding agent used for reaction, selected from the group comprising PPh$_3$, P(Cy)$_3$, Josiphos, Xantphos, dppe, dppp, dppf or the binding agent is Xantphos.

11. A process according to claim 1, wherein molar amounts of ligand from 0.5 to 2 times the molar amount of Palladium catalytic precursor are used.

12. A process according to claim 1, wherein molar amounts of ligand of about 0.5 times the molar amount of Palladium acetate catalytic precursor are used.

13. A process according to claim 1, wherein the reaction is conducted at between 60° C. and 140° C., or at between 80° C. and 120° C.

14. A process according to claim 1, wherein the reaction is conducted at between 85° C. and 100° C.

15. A process according to claim 1, wherein the reaction is conducted for between 16 to 30 hours.

16. A process according to claim 1, wherein the reaction is conducted for between 18 to 20 hours.

17. A process according to claim 1, wherein the reaction is conducted in an anhydrous milieu.

18. A process according to claim 1, wherein 1-(6-methylpyridin-3-yl)ethanone of formula (II):

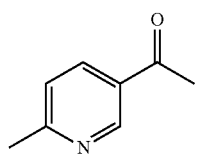

(II)

is obtained by conversion of the intermediate 5-ethynyl-2-methylpyridine of formula (IV):

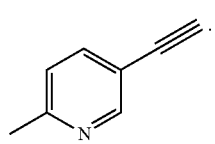

(IV)

19. A process according to claim 18, wherein the intermediate 5-ethynyl-2-methylpyridine of formula (IV):

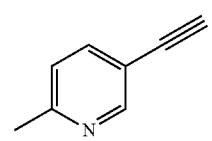

(IV)

is obtained by conversion of the intermediate 6-methylpyridin-3-yl trifluoromethansulfonate of formula (V):

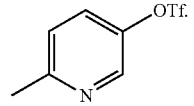

(V)

20. A process according to claim 1, wherein the reaction is conducted in DMF in the presence of potassium phosphate as a base, palladium(II) acetate as a catalytic precursor and Xantphos as a ligand.

21. A process according to claim 1, further comprising a purification step of compound 1-(6-methylpyridin-3-yl)-2-[4-(methylsulfonyl)phenyl] ethanone of formula (I) or a salt thereof:

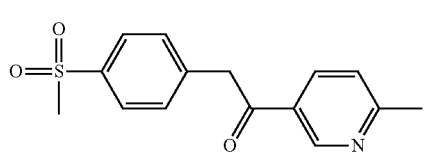

(I)

thus obtained.

22. A process according to claim 1, further comprising the step of using a Palladium catalyst.

23. A process according to claim 1, further comprising the step of using a Xantphos ligand.

* * * * *